United States Patent [19]
Hilpert et al.

[11] Patent Number: 5,919,956
[45] Date of Patent: Jul. 6, 1999

[54] PROCESS FOR THE $C_1$-HOMOLOGIZATION OF PROTECTED PHORENOL

[75] Inventors: Hans Hilpert, Reinach; Erich Widmer, Münchenstein, both of Switzerland

[73] Assignee: Roche Vitamins Inc., Parsippany, N.J.

[21] Appl. No.: 08/939,175

[22] Filed: Sep. 29, 1997

[30] Foreign Application Priority Data

Oct. 18, 1996 [EP] European Pat. Off. ............. 96116742

[51] Int. Cl.⁶ ............................. C07D 301/02; C07F 7/18
[52] U.S. Cl. ........................... 549/519; 549/332; 549/215
[58] Field of Search .............................................. 549/332

[56] References Cited

U.S. PATENT DOCUMENTS 4,000,131  12/1976  Rosenberger et al. .................. 260/240
5,126,128   6/1992  Mori et al. .

FOREIGN PATENT DOCUMENTS

WO 93/23388  11/1993  WIPO .

OTHER PUBLICATIONS

Barluenga et al., "Preparation of Disubstituted Epichlorohydrins with Total Diastereoselectivity. Transformation for α–Bromocarbonyl Compounds into Allyl Alcohols", Tetrahedron Letters, vol. 34, No. 19, pp. 3173–3176 (1993).

Barluenga et al, "The First Direct Preparation of Chiral Functionalised Ketones and their Synthetic Uses", J. chem. Soc. Chem. Commun. pp. 969–970 (1994).

H. Mayer, "Synthesis Of Optically Active Carotenoid and Related Compounds", Pure & Appl. Chem., 51:535–564 (1979).

Mitteilung, "Synthesis of optically active natural carotenoids and structurally related compounds", Helvetica Chimica Acta, vol. 63, pp. 1451–1455 1980.

Sadhu et al., "(Chloromethyl)lithium in an efficient conversion of carbonyl compounds to chlorohydrins or oxiranes", Tetrahedron Letters;, vol. 27, No. 7, pp. 795–798 (1986).

Tarhouni et al., "Monohalomethyllithium XCH2li: Stabilization of a potential synthetic reagent", Tetrahedron Letters, vol. 25, No. 8, pp. 835–838 1984).

Cainella et al., "Chemistry of Alpha–Halometal Compounds," Tetrahedron, vol. 27, pp. 6109–6114, 1971.

Greene, "Protection for the Hydroxyl Group Including 1,2–and 1,3–Diols," Protective Groups in Organic Synthesis, pp. 39–50, 1981.

March, "Carbon Attack by Organometallic Compounds," Advanced Organic Chemistry, pp. 836–842, 1977.

*Primary Examiner*—John M. Ford
*Assistant Examiner*—Ann M. Kessinger
*Attorney, Agent, or Firm*—George W. Johnston; Dennis P. Tramaloni; Joseph P. Kirk, Jr.

[57] ABSTRACT

A process for the manufacture of an optionally protected 4,8,8-trimethyl-1-oxaspiro[2.5]oct-4-en-6-ol (I) starting from protected 4-hydroxy-2,6,6-trimethyl-2-cyclohexen-1-one (II) comprises reacting the protected compound (II) with dihalomethyllithium and, if desired, cleaving off the protecting group from the thus-obtained protected 4,8,8-trimethyl-1-oxaspiro[2.5]oct-4-en-6-ol. The dihalomethyllithium can be produced in situ by reacting a dihalomethane with a lower alkyllithium in the presence of the compound of formula II. Preferably, protected (S)-4-hydroxy-2,6,6-trimethyl-2-cyclohexen-1-one is converted into protected (3S,6S)-4,8,8-trimethyl-1-oxaspiro[2.5]oct-4-en-6-ol in this manner. Both the starting material (II) and the end product (I) of the process in accordance with the invention are known, valuable intermediates for the manufacture of carotenoids.

30 Claims, No Drawings

PROCESS FOR THE C₁-HOMOLOGIZATION OF PROTECTED PHORENOL

BACKGROUND OF THE INVENTION

The present invention is concerned with a process for the conversion of a protected 4-hydroxy-2,6,6-trimethyl-2-cyclohexen-1-one (protected "phorenol") into the corresponding protected allylic epoxide, 4,8,8-trimethyl-1-oxaspiro[2.5]octa-4-en-6-ol, using a reagent which has never previously been used for this purpose. Both the starting material and the end product are known valuable intermediates for the manufacture of carotenoids.

The method hitherto used for the aforementioned conversion (a "C₁-homologization") involved dimethylsulphonium methylide as the reagent [see, for example, Pure & Appl. Chem. 51, 535–564 (1979), especially pages 546–547: 52+53→54; as well as Helv. Chim. Acta 63, 1451–1455 (1980), especially page 1452: 5→6]. This reagent is, however, troublesome to produce and yields as a byproduct the olfactorily annoying dimethyl sulphide, which are serious disadvantages.

SUMMARY OF THE INVENTION

The present invention is directed to a process for the manufacture of the optionally protected 4,8,8-trimethyl-1-oxaspiro[2.5]octa-4-en-6-ol starting from a protected phorenol using an alternative reagent, and thereby avoiding the aforementioned disadvantages associated with the use of dimethylsulphonium methylide. The desired process is achieved by using a dihalomethyllithium as the reagent in the C₁-homologization. Compared with the previously used reagent the use of the dihalomethyllithium also saves costs.

DETAILED DESCRIPTION OF THE INVENTION

The process in accordance with the invention for the manufacture of a protected 4,8,8-trimethyl-1-oxaspiro[2.5]octa-4-en-6-ol of the formula:

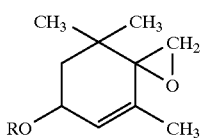

I wherein R is a protecting group for hydroxy, starting from a protected phorenol of the formula:

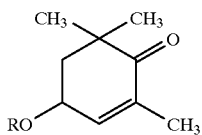

II wherein R is as above,
comprises reacting the protected phorenol with dihalomethyllithium.

The process of the invention also comprises a method for producing the unprotected trimethyl-1-oxaspiro[2.5]octa-4-en-6-ol of the formula:

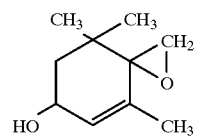

III which comprises reacting the protected phorenol of formula II with dihalomethyllithium to obtain the protected 4,8,8-trimethyl-1-oxaspiro[2.5]octa-4-en-6-ol of formula I, and then cleaving the protecting group, R, from the thus-obtained protected 4,8,8-trimethyl-1-oxaspiro[2.5]octa-4-en-6-ol of formula I under hydrolysis conditions to replace the protecting group with hydrogen.

The term "protecting group for hydroxy" is not critical and so embraces any conventional protecting groups for hydroxy groups useful in the present structural environment, especially protecting groups familiar from the carotenoid field. Etherified hydroxy groups especially come into consideration as protected hydroxy groups, RO—. These are, for example, $C_{1-5}$-alkoxy groups, preferably methoxy and ethoxy; mono and dialkoxyalkoxy groups containing up to 16 carbon atoms, preferably 1-methoxy-1-methylethoxy [hydroxy having the so-called isopropenyl methyl ether ("IPM") protecting group], or dimethoxymethoxy; arylalkoxy groups, preferably benzyloxy; tetrahydropyranyloxy; and silyloxy groups, preferably trimethylsilyloxy and phenyldimethylsilyloxy.

Where not further qualified herein, the term "alkyl" embraces straight-chain and branched groups, preferably with 1–5 carbon atoms, such as, for example, methyl, ethyl, n-propyl, isopropyl, tert.butyl and the like. This also applies to the alkyl moiety of each "alkoxy". Where an aryl group is present, this is preferably phenyl, which is optionally substituted, e.g., with one or more $C_{1-5}$-alkyl and/or nitro groups. However, unsubstituted phenyl is preferred.

The IPM and the trimethylsilyl ("TMS") protecting groups are especially preferred protecting groups.

The halogens of the dihalomethyllithium are not critical, and may be the same or different and are selected from fluorine, chlorine, bromine and iodine. The preferred dihalomethyllithium is bromochloromethyllithium.

Formulae I and II above are presented neutrally with respect to the isomeric form (configuration), but embrace all isomeric (especially optically isomeric) forms. In accordance with one embodiment of the process in accordance with the invention protected (S)-phorenol of formula II' is converted into protected (3S,6S)-4,8,8-trimethyl-1-oxaspiro[2.5]oct-4-en-6-ol of formula I' using the dihalomethyllithium:

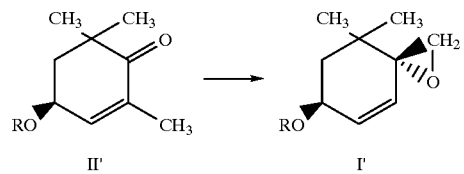

II'    I'

The C₁-homologization according to the process in accordance with the invention is preferably effected with dihalomethyllithium produced in situ, with a dihalomethane and a lower alkyllithium being reacted in the presence of the compound of formula II. The resulting dihalomethyllithium reacts in accordance with the invention with the protected phorenol of formula II. Fluorine, chlorine, bromine or iodine is suitable as the halogen for the dihalomethane [Hal in $CH_2(Hal)_2$], with the two halogen atoms being the same or different. Bromochloromethane is especially preferred in this case. As "lower alkyl" of the lower alkyllithium there comes into consideration especially straight-chain or branched alkyl with up to 8 carbon atoms, such as, for example, methyl, ethyl, n-propyl, isopropyl, n-butyl, isobutyl, sec.butyl, tert.butyl, pentyl, hexyl, heptyl and octyl. $C_{1-4}$-Alkyl is especially preferred, with n-butyl- or hexyllithium being a particularly preferred lower alkyllithium. This is usually used in solution in a lower alkane, preferably hexane. The reaction of the dihalomethane with the lower alkyllithium produces the dihalomethyllithium, which thereupon reacts with the protected phorenol in the same reaction medium. For example, chloromethyllithium is produced from bromochloromethane and n-butyllithium, with n-butyl bromide being produced as the byproduct.

The $C_1$-homologization (and the in situ production of the dihalomethyllithium) is, moreover, conveniently carried out in an aliphatic or cyclic ether as the solvent at temperatures of about –20° C. to about –120° C., preferably from about –60° C. to about –80° C. The solvent is, for example, diethyl ether or tert.butyl methyl ether or, respectively, tetrahydrofuran or dioxan. The reaction is preferably carried out in tetrahydrofuran.

The amount of dihalomethyllithium used in the reaction of the invention is not critical, so long as a detectable amount of the epoxidized product is formed. Preferably, from 1 to 2 equivalents of dihalomethyllithium is used per equivalent of protected phorenol. When the dihalomethyllithium is generated in situ, preferably 1 to 2, more preferably about 1.1, equivalents of the dihalomethane as well as preferably about 1 to 2, more preferably about 1.5, equivalents of the lower alkyllithium are used per equivalent of protected phorenol.

After completion of the epoxidation, which normally takes about 30 to about 60 minutes, the working up of the mixture may be carried out by conventional means. Preferably, the reaction mixture is warmed to the temperature range of about –70 to about –30° C., diluted with water or aqueous sodium chloride solution, especially saturated sodium chloride solution, and extracted with a suitable organic solvent, conveniently that used for the reaction. After evaporation of the solvent and optional crystallization and/or other purification methods, the product of formula I is obtained in good purity.

As a further step in the process of the invention, the protecting group present in the product obtained can be cleaved off and replaced by hydrogen according to methods known per se, e.g., by hydrolysis with acid or base. The hydrolysis conditions used to cleave the protecting group are not critical. Any conventional hydrolysis conditions may be used in accordance with the present invention. Thereby, 4,8,8-trimethyl-1-oxaspiro[2.5]oct-4-en-6-ol, the compound of formula III is obtained. Thus, the present invention also comprises a method of making a compound of formula III from a compound of formula II by reacting the compound of formula II with a dihalomethyllithium to obtain a compound of formula I, and subsequently cleaving the protecting group for hydroxy, R, from the compound of formula I under hydrolysis conditions to produce the compound of formula III.

The compound of formula I can be converted according to methods known per se in several reaction steps into useful end products, e.g., carotenoids and pharmaceuticals [see, for example, Pure & Appl. Chem. 51, 535–564 (1951)].

The invention is illustrated by the following Examples.

EXAMPLE 1

Preparation of Acetone Methyl[(3S,6S)-4,8,8-trimethyl-1-oxaspiro[2.5]oct-4-en-6-yl]acetal A solution of 2.00 g of (S)-4-(1-methoxy-1-methylethoxy)-2,6,6-trimethyl-2-cyclohexen-1-one and 1.25 g of bromochloromethane in 20 ml of tetrahydrofuran, cooled to –80° C., was treated within 30 minutes with 8.3 ml of a 1.6 molar solution of n-butyllithium in hexane. The reaction mixture was then warmed to –35° C. and treated with 15 ml of semi-saturated sodium chloride solution. The organic phase was separated, dried over anhydrous sodium sulphate and concentrated under reduced pressure. This gave 2.1 g of acetone methyl[(3S,6S)-4,8,8-trimethyl-1-oxaspiro [2.5]oct-4-en-6-yl]acetal as a white solid, m.p. 53–59° C.; after recrystallization from methanol, m.p. 65.2–66.8° C.

EXAMPLE 2

Preparation of (3R,6S)- and (3S,6S)-Trimethyl-(4,8, 8-trimethyl-1-oxaspiro-[2.5]octa-4-en-6-yloxy)-silane Starting from (4S)-4-Hydroxy-2,6,6-trimethyl-2-cyclohexen-1-one via its TMS-protected Form (One Pot Process)

A solution of 22.1 g of (4S)-4-hydroxy-2,6,6-trimethyl-2-cyclohexen-1-one in 200 ml of tetrahydrofuran, cooled to –80° C., was treated within 40 minutes with 90 ml of a 1.6 molar solution of n-butyllithium in hexane and thereafter treated within 10 minutes with 20 ml of chlorotrimethylsilane. Then, 10.5 ml of bromochloromethane were added dropwise during 10 minutes and 134.5 ml of the 1.6 molar solution of n-butyllithium in hexane were added dropwise during one hour at –80° C., and the mixture was stirred for 20 minutes. The reaction mixture was warmed to –30° C. and treated with 200 ml of semi-saturated sodium chloride solution. Then, the organic phase was separated, dried over anhydrous sodium sulphate and concentrated under reduced pressure. In this manner there were obtained 33.6 g of a thin-layer chromatographically pure mixture of (3R,6S)- and (3S,6S)-trimethyl-(4,8,8-trimethyl-1-oxaspiro[2.5]oct-4-en-6-yloxy)-silane. Mass spectrum: 240/3, M$^+$; tlc (SiO$_2$, hexane/ethyl acetate 1:1): R$_f$=0.70.

We claim:
1. A process for the manufacture of a protected 4,8,8-trimethyl-1-oxaspiro[2.5]oct-4-en-6-ol of the formula:

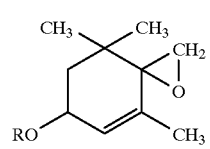

wherein R is a protecting group for hydroxy, which process comprises reacting a protected 4-hydroxy-2, 6,6-trimethyl-2-cyclohexen-1-one of the formula:

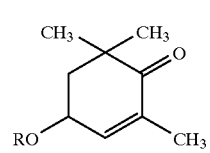

wherein R is as above,
with a dihalomethyllithium to obtain the compound of formula I.

2. The process of claim 1 wherein the dihalomethyllithium is produced in situ in the presence of the compound of formula II by reacting a dihalomethane with a lower alkyllithium.

3. The process of claim 2 wherein the dihalomethane and the lower alkyllithium are each independently present in an amount from about 1 to about 2 equivalents per equivalent of the compound of formula II.

4. The process of claim 3 wherein the dihalomethane is bromochloromethane.

5. The process of claim 4 wherein the lower alkyllithium is n-butyllithium or hexyllithium.

6. The process of claim 5 wherein the reaction is carried out in a solvent which is an aliphatic or cyclic ether.

7. The process of claim 6 wherein the solvent is tetrahydrofuran.

8. The process of claim 7 wherein the reaction is carried out at a temperature in the range from about −20° C. to about −120° C.

9. The process of claim 8 wherein the reaction is carried out at a temperature in the range from about −60° C. to about −80° C.

10. The process of claim 9 wherein the protecting group, R, is isopropenyl methyl ether or trimethylsilyl.

11. The process of claim 1 wherein the compound of formula II is:

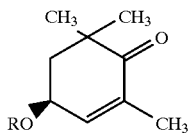

II' and the compound of formula I is:

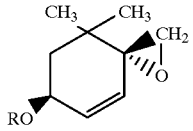

I' wherein R is as in claim 1.

12. The process of claim 11 wherein the dihalomethyllithium is produced in situ in the presence of the compound of formula II' by reacting a dihalomethane with a lower alkyllithium.

13. The process of claim 12 wherein the dihalomethane and the lower alkyllithium are each independently present in an amount from about 1 to about 2 equivalents per equivalent of the compound of formula II'.

14. The process of claim 13 wherein the dihalomethane is bromochloromethane.

15. The process of claim 14 wherein the lower alkyllithium is n-butyllithium or hexyllithium.

16. The process of claim 15 wherein the reaction is carried out in a solvent which is an aliphatic or cyclic ether.

17. The process of claim 16 wherein the solvent is tetrahydrofuran.

18. The process of claim 17 wherein the reaction is carried out at a temperature in the range from about −20° C. to about −120° C.

19. The process of claim 18 wherein the reaction is carried out at a temperature in the range from about −60° C. to about −80° C.

20. The process of claim 19 wherein the protecting group, R, is isopropenyl methyl ether or trimethylsilyl.

21. A process for the manufacture of an epoxide, 4,8,8-trimethyl-1-oxaspiro[2.5]oct-4-en-6-ol, which process comprises reacting a protected 4-hydroxy-2,6,6-trimethyl-2-cyclohexen-1-one of the formula:

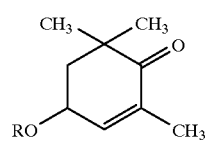

II wherein R is a protecting group for hydroxy,
with a dihalomethyllithium to obtain a compound of the formula:

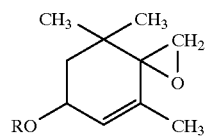

I wherein R is as above,
and thereafter cleaving the protecting group, R, from the compound of formula I under hydrolysis conditions to produce the epoxide.

22. The process of claim 21 wherein the dihalomethyllithium is produced in situ in the presence of the compound of formula II by reacting a dihalomethane with a lower alkyllithium.

23. The process of claim 22 wherein the dihalomethane and the lower alkyllithium are each independently present in an amount from about 1 to about 2 equivalents per equivalent of the compound of formula II.

24. The process of claim 23 wherein the dihalomethane is bromochloromethane.

25. The process of claim 24 wherein the lower alkyllithium is n-butyllithium or hexyllithium.

26. The process of claim 25 wherein said process is carried out in a solvent which is an aliphatic or cyclic ether.

27. The process of claim 26 wherein the solvent is tetrahydrofuran.

28. The process of claim 27 wherein the reaction of the compound of formula II with the bromochloromethane is carried out at a temperature in the range from about −20° C. to about −120° C.

29. The process of claim 28 wherein the reaction of the compound of formula II with the bromochloromethane is carried out at a temperature in the range from about −60° C. to about −80° C.

30. The process of claim 29 wherein the protecting group, R, is isopropenyl methyl ether or trimethylsilyl.

* * * * *